(12) United States Patent
Dolzan et al.

(10) Patent No.: US 9,883,971 B2
(45) Date of Patent: Feb. 6, 2018

(54) COMBINED OPHTHALMIC LASER DEVICE

(71) Applicant: OPTOTEK D.O.O., Ljubljana (SI)

(72) Inventors: Ales Dolzan, Litija (SI); Klemen Kunstelj, Skofja Loka (SI); Boris Vedlin, Ljubljana (SI); Andrej Vrecko, Ljubljana (SI); Matjaz Zalar, Višnja Gora (SI)

(73) Assignee: OPTOTEK D.O.O., Ljubljana (SI)

( * ) Notice: Subject to any disclaimer, the term of this patent is extended or adjusted under 35 U.S.C. 154(b) by 0 days.

(21) Appl. No.: 14/439,663

(22) PCT Filed: Oct. 29, 2013

(86) PCT No.: PCT/SI2013/000064
§ 371 (c)(1),
(2) Date: Apr. 30, 2015

(87) PCT Pub. No.: WO2014/070119
PCT Pub. Date: May 8, 2014

(65) Prior Publication Data
US 2015/0297408 A1    Oct. 22, 2015

(30) Foreign Application Priority Data
Oct. 30, 2012    (SI) .................................... 201200328

(51) Int. Cl.
*A61F 9/008*    (2006.01)
*A61F 9/007*    (2006.01)

(52) U.S. Cl.
CPC ........ *A61F 9/00823* (2013.01); *A61F 9/0084* (2013.01); *A61F 9/00781* (2013.01); *A61F 2009/0087* (2013.01); *A61F 2009/00868* (2013.01); *A61F 2009/00876* (2013.01); *A61F 2009/00889* (2013.01); *A61F 2009/00891* (2013.01)

(58) Field of Classification Search
CPC . A61F 9/00823; A61F 9/00781; A61F 9/0084
USPC ....................................................... 606/3–4
See application file for complete search history.

(56) References Cited

U.S. PATENT DOCUMENTS

2004/0215175 A1* 10/2004 Feklistov ................ A61F 9/008
606/4

FOREIGN PATENT DOCUMENTS

CH    EP 2384727 A1 *  11/2011    ........... A61F 9/0084
EP         238472           11/2011
(Continued)

*Primary Examiner* — Lynsey Eiseman
*Assistant Examiner* — Dacheng Xie
(74) *Attorney, Agent, or Firm* — Gina M. Lupino

(57) ABSTRACT

The object of the invention is a laser device for eye surgery used by ophthalmologists in the treatment with capsulotomy and iriditomy, and a device for selective laser trabeculoplasty. The essence of the ophthalmic laser combined device of the invention lies in that it has one single laser with one optical axis for both wavelengths; the basic wavelength of 1064 nm and the frequency doubled wavelength of 532 nm. Switching between both wavelengths is carried out by a polarization orientation switch. Frequency doubling is inactive at the wavelength of 1064 nm and it is active for the wavelength of 532 nm. At the wavelength of 532 nm additional optical elements for attenuating and collimating the laser pulse are switched on.

17 Claims, 3 Drawing Sheets

(56) References Cited

FOREIGN PATENT DOCUMENTS

Figure 1:
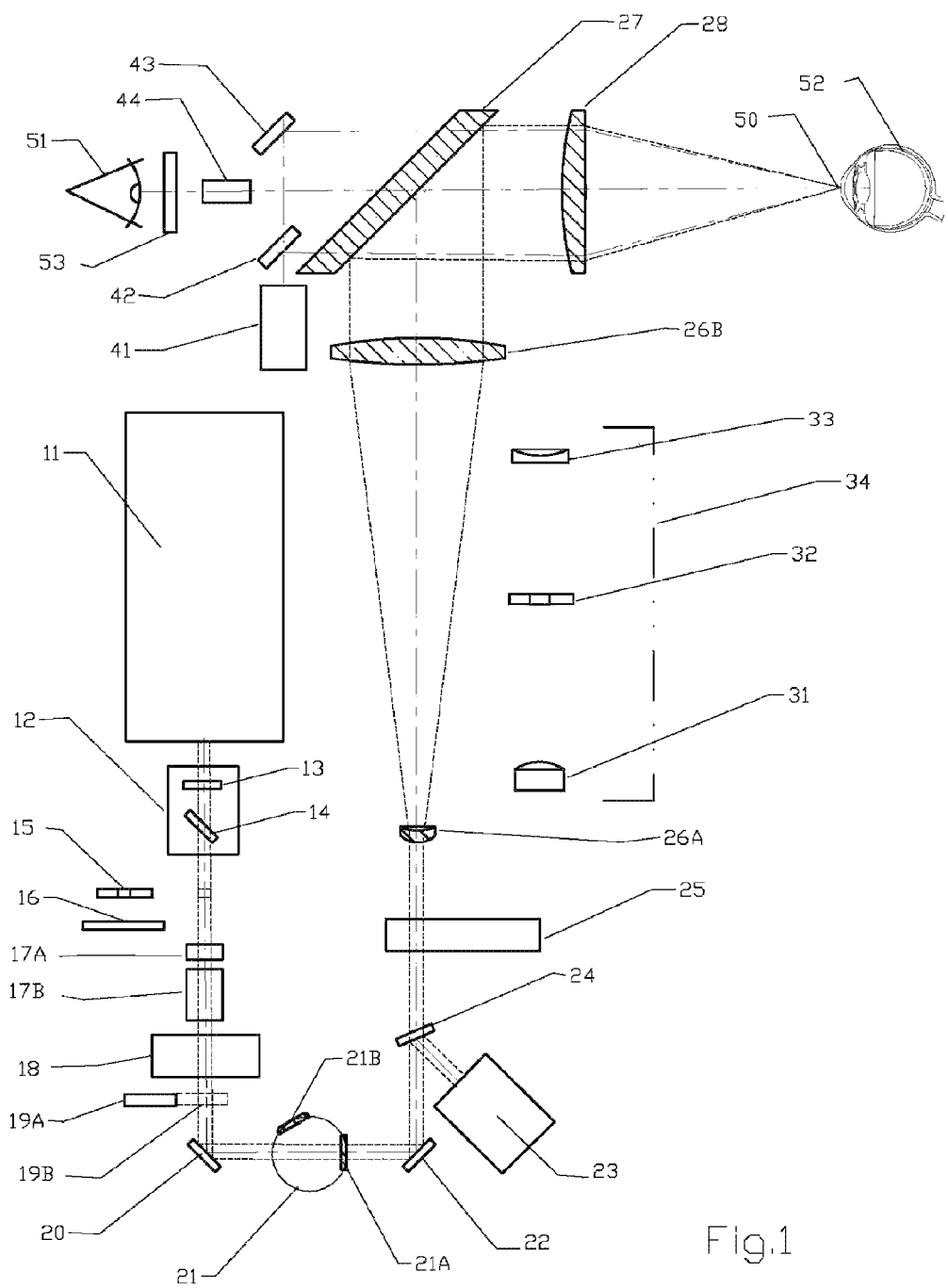

WO WO2004/027487 4/2004
WO WO2007/043052 4/2007

* cited by examiner

COMBINED OPHTHALMIC LASER DEVICE

The object of the invention is a laser device for eye surgery used by ophthalmologists in the treatment with capsulotomy and iriditomy, and a device for selective laser trabeculoplasty.

The technical problem solved by the present invention is such a construction of the device that makes it possible to perform both types of surgeries by using one laser ophthalmologic system, namely a treatment with capsulotomy and iriditomy at a laser wavelength of 1064 nm and a treatment with selective laser trabeculoplasty at a frequency doubled wavelength of 532 nm. The device is designed to have only one laser with one optical axis of a laser beam with a basic wavelength of 1064 nm, which laser beam will be converted by the device into a wavelength of 532 nm by means of a suitable beam switch and a module for frequency doubling. The solution of the invention should allow conversion of any wavelength of the basic laser beam into any desired wavelength.

One of frequent eye diseases is cataract which occurs as opacification of the lens inside the eye. A growing number of people suffer from this disease with biological aging. In cataract surgery the original eye lens lying in a bag (capsule) is removed. An artificial lens replacing the original one is inserted into the capsule and enables normal vision. After cataract surgery up to 30% of patients develop secondary cataract within a period of weeks, months or years, which is experienced as opacification in the capsule containing the artificial lens. Surgery of secondary cataract is performed with a photodisruptor containing a Nd:YAG pulsed laser so that optical breakdown is used to open the capsule and normal vision is achieved through the opening in the capsule. An example of such ophthalmic laser system is disclosed in U.S. Pat. Nos. 6,325,792 and 7,393,349.

Another frequent eye disease is glaucoma, in which the eye nerve is damaged at a site where it exits the eye. Damages of the eye nerve cause irreversible vision impairment. The frequency of glaucoma increases with ageing and more than 4% of population experience this disorder at the age of 80. The damage of the eye nerve in glaucoma is most often related to high intraocular pressure that occurs due to a too slow flow of the aqueous humour through trabecular meshwork. If the intraocular pressure is too high, the optic nerve gets mechanically damaged, which results in degeneration of nerve fibres. Due to undesired side effects of treatment with medicines, doctors and equipment developers have searched for a different solution. A treatment technique by means of laser is known as laser trabeculoplasty. This technique was discovered by Latina and is disclosed in U.S. Pat. No. 5,549,596 of the owner The General Hospital Corporation. Latina described use of a pulsed frequency doubled Nd:YAG laser for laser trabeculoplasty.

Selective laser trabeculoplasty (SLT) is an improvement over a previously used technique referred to as argon trabeculoplasty. The method of argon trabeculoplasty uses a thermal effect to coagulate the trabecular meshwork and thus enhance the flow of aqueous humour. Due to thermal effects the argon trabeculoplasy method irreversibly damages the meshwork and can be applied only once or twice at the most.

Surgery with selective laser trabeculoplasty uses a pulse laser with pulses shorter than 5 ns, in which thermal effects are negligible and can be repeated for an optional number of times.

Hitherto known solutions used for a photodisruptor and a selective laser trabeculoplasty (SLT) devices make use of two various devices, wherein each device individually performs one of the operations.

In its patent application WO 2004/027487 the company Ellex disclosed an optical system combining operations of two devices, of a photodisruptor and a laser device for selective laser trabeculoplasty in one single device. Such an ophthalmologic laser system emits a first wavelength suitable for secondary cataract surgery and a second wavelength suitable for selective laser trabeculoplasty surgery. An Nd:YAG laser source with a Q switch generates a short pulse with a pulse length shorter than 5 ns at a wavelength of 1064 nm. To set the energy in the photodisruptor mode a plate λ/2 13 is used which linearly attenuates pulse energy by rotation between 0.3 and 10 mJ. By rotating the plate λ/2 13 polarization rotates in a way that a laser beam deflects from the polarizer in the optical path to another axis intended to generate a frequency doubled pulse for selective laser trabeculoplasty. Rotation of polarisation and a different deflection on the polarizer make this solution operative in two different optical axes, in the first axis in the photodisruptor mode and in the second axis in the SLT mode. In this solution, the basic laser beam is redirected by a deflection on the polarizer to another optical axis, where frequency doubling of the laser beam is performed. In this way the second optical axis is used for the operation in the SLT mode.

The present invention has one optical axis both for the operation in the photodisruptor mode and for the operation in the SLT mode.

A common characteristic of all described systems is that two separate units or two optical axes within one device are needed, so that one optical axis operates in the photodisruptor mode and the second axis operates in the selective laser trabeculoplasty mode.

A problem that has remained unsolved is a combined device for a photodisruptor and for a selective laser trabeculoplasty, where operation of the ophthalmic laser device would be enabled in both modes, i. e. in the photodisruptor mode and in the SLT mode, by switching optical elements from the optical axis and back.

The essence of the ophthalmic laser combined device of the invention lies in that it has one single laser with one optical axis for both wavelengths; the basic wavelength of 1064 nm and the frequency doubled wavelength of 532 nm. Switching between both wavelengths is carried out by means of a polarization orientation switch, wherein for operation at a wavelength of 532 nm frequency doubling is switched on and for operation at a wavelength of 1064 nm frequency doubling is inactive.

The ophthalmic laser combined device of the invention will be described in more detail in the continuation with reference to the following figures in which FIG. 1—shows a block diagram of the device in a photodisruptor mode FIG. 2—shows a block diagram of the device in an SLT mode FIG. 3—shows a block diagram of an energymeter The ophthalmic laser combined device is embodied on one laser source 11 emitting short pulses with high peak power at the first wavelength of 1064 nm that are attenuated by an attenuator 12 and collected to a patient's eye 52 by way of collimation optic. In the same optical axis of the laser beam having the basic wavelength of 1064 nm an optical system with another wavelength of 532 nm is provided. Said optical system comprises attenuators 12 and 18, non-linear crystals 17A and 17B for frequency doubling, which change the first wavelength to the second one, and collimation optic that collects the laser pulse of the second wavelength in the patient's eye 52.

The ophthalmic laser combined device operating in the photodisruptor mode in FIG. 1 has a Nd:YAG laser source 11 that emits a short pulse of a length of about 5 ns in the infrared region at a wavelength of 1064 nm, which pulse travels through the energy attenuator 12, where, output energy is regulated by means of a polarization rotator 13 and a fixed polarizer 14. A polarization switch 16 is represented by plate λ/2 13 that gets displaced from the optical axes together with an aperture 15 so that the laser pulse can travel without frequency doubling through the non-linear crystals 17A and 17B. The pulse travels from the crystal 17B through a pass filter 19B that transmits the infrared wavelength, then deflects from a mirror 20, continues through a correction optical system 21 and deflects from a second mirror 22. The pulse goes through a beam splitter 24, where a small portion thereof gets deflected towards an energymeter 23 and a majority of the pulse goes through a shutter 25 that performs safety function of blocking the optical path. Then it goes through a small part 26A to a large part 26B of a telescope that expands the laser beam and deflects it via a dichroic mirror 27 and by means of a lens 28 collects the laser pulse in a focus 50 of the optical system, where optical breakdown is achieved. Optical breakdown is used for capsule surgery in order to remove secondary cataract. For an ophthalmologist 51 to be able to monitor where the optical breakdown will appear in laser focus 50 in the patient's eye 52, a red diode 41 is switched on and projects on two branches, wherein a first one deflects from a beam splitter 42 and a second one from a mirror 43 and both together are then projected into the same spot, in which the focus 50 of the optical system is. A filter 53 prevents a part from the infrared laser pulse to deflect into the eye of the ophthalmologist 51.

The ophthalmic laser combined device has an integrated laser 11 of Nd:YAG type, pumped by a flash or diode that emits laser pulses with a wavelength of 1064 nm for the first wavelength with a constant orientation of polarization. When the laser 11 emits a short and linearly polarized pulse, the latter goes through the attenuator 12. The plate λ/2 13 and the polarizer 14 are integrated in the attenuator 12, wherein the plate λ/2 13 has a characteristic of rotating the input plane of linear polarization. A rotation of the plate λ/2 13 determines how much pulse will be transmitted through the polarizer 14, which enables a linear setting of energy. The position of rotation of the plate λ/2 13 can be set electromechanically so that linear setting of energy of the photodisruptor is enabled. The second attenuator 18 is inactive in this operation mode.

Figure 2:
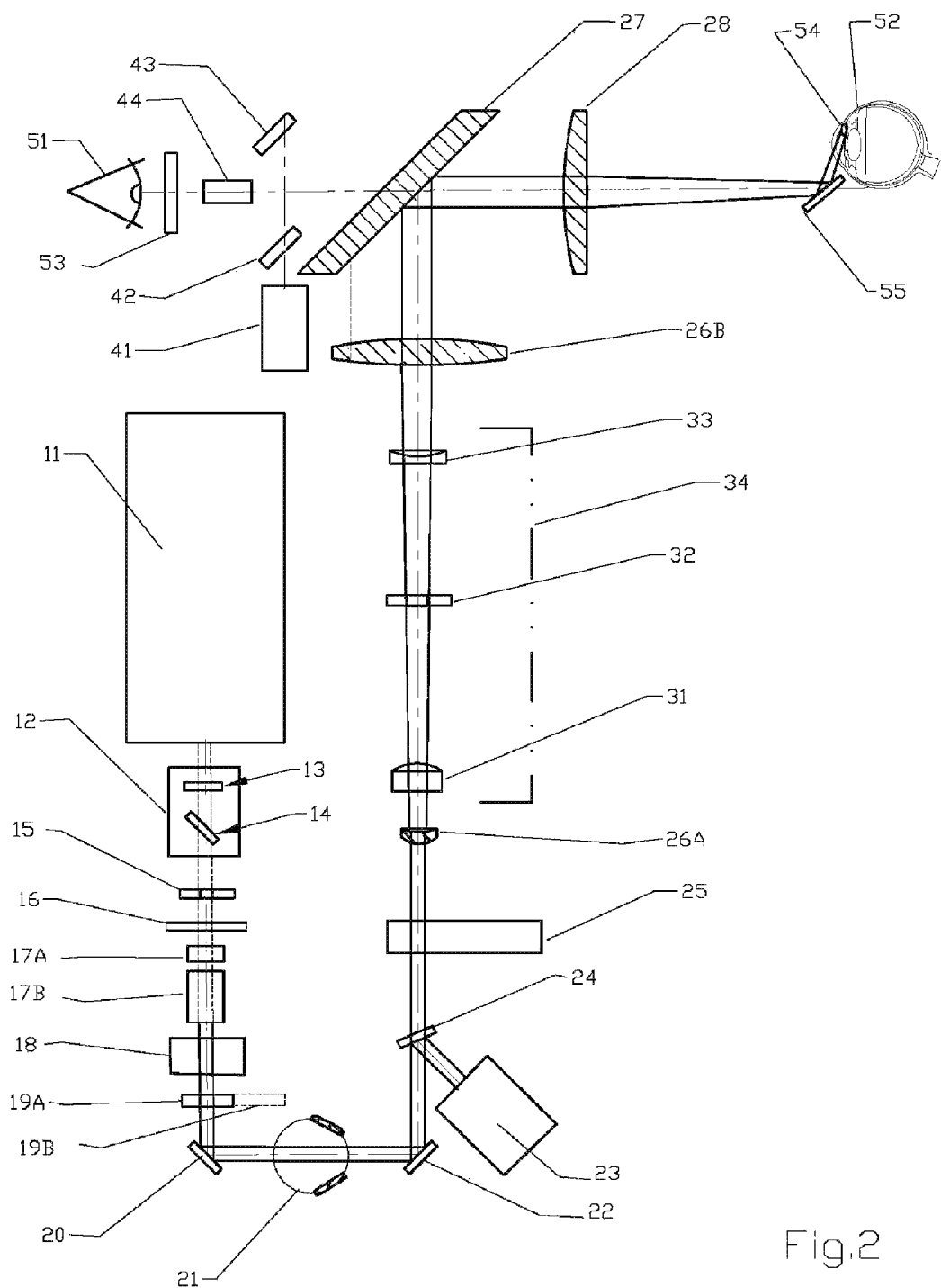
Figure 3:
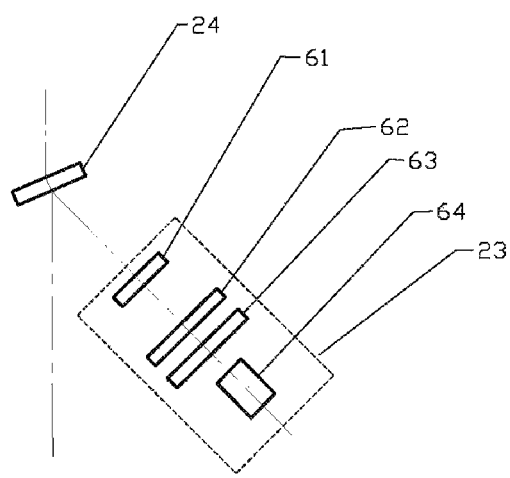

The ophthalmic laser combined device that operates in the SLT mode from FIG. 2 comprises the laser source 11 that, emits a short pulse of a length of about 5 ns that goes through the energy attenuator 12, where output energy is linearly set by means of the polarization rotator 13 and the fixed polarizer 14. The laser pulse having a wavelength of 1064 nm is frequency doubled by switching on the polarization switch 16 at the transition through the non-linear crystals 17A and 17B to a wavelength of 532 nm. The attenuator 18 attenuates the laser pulse by means of absorption filters. The remainder of the wavelength of 1064 nm that was not converted in the non-linear crystal 17A and 17B gets absorbed in the filter 19A. The wavelength of 532 nm that was transmitted gets reflected from the mirror 20, goes past the inactive correction optical system 21 and deflects from the mirror 22 to the beam splitter 24, where a small portion of the pulse is detected by the energymeter 23. A larger portion of the pulse goes through the shutter 25 having a safety function of blocking the optical path, and through the smaller part of the telescope 26A. The laser beam collimates in a first switch lens 31, travels through the correction optic 32 to a second switch lens 33 and then to the large part of the telescope 26B, where the collimated laser beam deflects via the dichroic mirror 27 and gets collected by means of the lens 28 in the focal plane in a spot 54. The dichroic mirror 27 deflects the first and the second wavelength of the laser pulse, enables observation in the visible part of the spectrum of the eye 52 and transmits the wavelength for both red navigation diodes 41 and 44. The spot of the laser beam is mirrored by means of an accessory lens—mirror 55 to trabecular meshwork in the iridocorneal angle, where surgery is performed. To determine the site of surgery the red diode 44 is switched on and its light reflects into the focus 54. The correction optic 32 is in the shape of an aperture or another optical system in order to enhance the profile of a laser pulse. The ophthalmologist's eye is protected against the reflected portion of the visible pulse by the filter 53.

In the photodisruptor mode, the linear polarization is rotated by the polarization switch 16 in a way that the laser pulse travels through the non-linear crystals 17A and 17B without conversion. Input polarization is selected by means of the switch 16 in a way that the condition for frequency doubling is not met.

When the device operates in the SLT mode, the laser 11 emits a pulse that travels through the frequency doubling module comprised of one or two non-linear crystals 17A and 17B, where the laser pulse gets frequency doubled. The linear attenuator 12 is arranged in the area of maximum transmission in order to allow as stable frequency doubling on the non-linear crystals 17A and 17B as possible. Downstream of the frequency doubling module the second attenuator 18 is arranged, which is provided with embedded discrete absorption filters that are not dependent on polarization and are electronically controlled. As absorption filters have discrete values, the first attenuator 12 is used for linear regulation of the pulse energy, which linearly attenuates the pulse and bridges the difference in transmission between individual discrete transmission filters.

When the device operates in the SLT mode, the plate λ/2 13 in the polarization switch 16 is rotated in a way that the condition for frequency doubling in the non-linear crystals 17A and 17B is met and the laser pulse gets converted to the second wavelength of 532 nm.

The optical system makes use of the frequency doubling module comprised of one or two non-linear crystals 17A, 17B. In the case when one non-linear crystal is used, doubling stability is poorer than in the case when two non-linear crystals 17A, 17B are used. An advantage of use of one non-linear crystal is preservation of linear polarization, which allows use of the second linear attenuator 18 that functions on the basis of polarization, the same as the attenuator 12.

An advantage of use of two non-linear crystals 17A, 17B is better energy stability in frequency doubling, whereas a drawback is undefined output polarization. When two non-linear crystals 17A, 17B are used, it is necessary to arrange discrete or linear absorption filters that are independent on polarization plane into the attenuator 18. The first attenuator 12 is used for linear regulation of pulse energy that linearly attenuates the pulse and bridges the difference in transmission between individual discrete transmission filters, wherewith perfectly linear regulation of the pulse energy is achieved over the entire energy area.

In the photodisruptor mode having the first wavelength of 1064 nm, the bandpass filter 19B is switched on and transmits the first wavelength of 1064 nm and absorbs the second wavelength of 532 nm. In the SLT mode having the second wavelength of 532 nm, the bandpass filter 19A is used which transmits the wavelength of 532 nm and absorbs the first one. The bandpass filters contribute to an undisturbed operation without a presence of disturbing wavelengths.

To measure pulse energy small reflection is used on the beam splitter 24 which diverts part of the pulse energy to the energymeter 23. For both operation modes, i. e. the photodisruptor mode and the SLT mode, one single energymeter 23 is used that uses only one diode 64 for both modes. Upstream the diode 64 a pass filter 62 is arranged that transmits the first and the second wavelength and blocks other wavelengths. The influence of ambient light is thus filtered. The function of one filter can be replaced by two separate filters 62 and 63.

Switching of the optical system for the photodisruptor mode and the SLT mode, for the first and the second wavelength, is carried out by electromechanical and electronic control and microprocessor control.

The optical modules 15 and 32 made of a combination of lenses and apertures modify the profile of energy distribution within the laser pulse of the first and the second wavelength, so that uniform beam profile distribution is generated from the Gaussian profile.

Optical elements from the module for correction lenses 21 that contains the lenses 21A and 21B can be built into the mechanical system of the second attenuator 18 so that individual lenses are added apart from discrete filters. For the operation in the SLT mode with electronic control an adequate value of the discrete filter is used, whereas a suitable lens 21A and 21B is selected for the operation in the photodisruptor mode.

The invention claimed is:

1. An ophthalmic laser combined device operable in a photodisruptor mode or a selective laser trabeculoplasty (SLT) mode, the device comprising:
    a laser beam source for emitting a short pulsed laser beam comprising a plurality of beam pulses comprising a high peak power at a first wavelength comprising 1064 nm, wherein the laser beam source comprises a Nd:YAG laser source comprising a flash or diode pumping,
    a plurality of attenuators (12, 18) configured to control energy of the laser beam pulses,
    a frequency doubling module (17A, 17B) for converting the first wavelength to a second wavelength comprising 532 nm,
    first and second mirrors (20, 22),
    a beam splitter (24) comprising an energymeter (23),
    a beam shaping module comprising:
        a telescope comprising a plurality of telescope components (26A, 26B),
        a dichroic mirror (27), and
        a lens (28) for directing the beam to a target,
    an optical path for the laser beam pulses,
    a λ/2 plate (13), and
    optical shifting components comprising:
        an aperture (15) moveable in and out of the optical path,
        a polarization switch (16) moveable in and out of the optical path, for moving the optical shifting components in and out of the optical path and changing the first wavelength to the second wavelength,
        a plurality of pass filters (19A, 19B) configured to be activated and deactivated and moveable in and out of the optical path,
        a plurality of switch lenses (31, 33) moveable in and out of the optical path, and
        correction optics (32) moveable in and out of the optical path, and
    wherein insertion of the polarization switch into the optical path activates the λ/2 plate (13) and the frequency doubling module (17A, 17B) and converts the first wavelength to the second wavelength.

2. The ophthalmic laser combined device of claim 1, further comprising non-linear crystals (17A, 17B), wherein
    the plurality of pass filters (19A, 19B) comprises a first pass filter (19A) and a second pass filter (19B), and
    plurality of switch lenses (31, 33) comprises a first switch lens (31) and a second switch lens (33), and
wherein during operation in the photodisruptor mode,
    the aperture (15) is located out of the optical path,
    the polarization switch (16) is located out of the optical path,
    the first pass filter (19A) is located out of the optical path,
    the second pass filter (19B) is located in the optical path,
    the first switch lens (31) is located out of the optical path,
    the correction optics (32) are located out of the optical path,
    the second switch lens (33) is located out of the optical path, and
    the laser beam pulses travel through the non-linear crystals (17A) and (17B) without frequency doubling so that the pulses comprise a wavelength of 1064 nm.

3. The ophthalmic laser combined device of claim 1, wherein
    the plurality of pass filters (19A, 19B) comprises a first pass filter (19A) and a second pass filter (19B),
    plurality of switch lenses (31, 33) comprises a first switch lens (31) and a second switch lens (33),
    the plurality of telescope components comprises a first telescope component and a second telescope component,
    the frequency doubling module (17A, 17B) comprises non-linear crystals (17A, 17B), and
wherein during operation in the SLT mode,
    the aperture (15) is located in the optical path,
    the polarization switch (16) is located in the optical path,
    the first pass filter (19A) is located in the optical path and the second pass filter (19B) is located out of the optical path,
    the first switch lens (31) is located in the optical path between the first telescope component (26A) and the second telescope component (26B),
    correction optics (32) is located in the optical path between the first telescope component (26A) and the second telescope component (26B),
    the second switch lens (33) is located in the optical path between the first telescope component (26A) and the second telescope component (26B), and
    the non-linear crystals (17A) and (17B) convert the laser beam pulses into the second wavelength.

4. The ophthalmic laser combined device of claim 1, wherein the plurality of attenuators (12, 18) comprises a first attenuator (12) and a second attenuator (18) disposed downstream of the laser beam source, for controlling the energy of the first and second wavelengths.

5. The ophthalmic laser combined device of claim 1, wherein the energymeter (23) is operable in the photodisruptor mode or the SLT mode.

6. The ophthalmic laser combined device of claim 1, further comprising a control system for moving the optical shifting components in and out of the optical path and switching the first and the second wavelength.

7. The ophthalmic laser combined device of claim 1, wherein the optical shifting components are embedded in the second attenuator.

8. The ophthalmic laser combined device of claim 1, wherein
the optical shifting components are disposed between the plurality of telescope components and a focus, and
the optical shifting components collimate and reflect the laser beam pulse to a focal plane for the second wavelength.

9. The ophthalmic laser combined device of claim 1, further comprising non-linear crystals (17A, 17B), wherein
the polarization switch is configured to switch the device between the operation modes in a way that
in a first wavelength photodisruptor mode the laser pulse travels through non-linear crystals without conversion, and
in the SLT mode the laser pulse is converted in the non-linear crystals to the second wavelength.

10. The ophthalmic laser combined device of claim 1, wherein the plurality of pass filters (19A, 19B) comprises a first pass filter (19A) and a second pass filter (19B), and wherein
the first pass filter is configured to activate the first wavelength and
the second pass filter is configured to activate the second wavelength.

11. The ophthalmic laser combined device of claim 1, wherein one of the attenuators of the plurality of attenuators is configured to linearly set energy values of the laser beam pulses of the first wavelength and the second wavelength.

12. The ophthalmic laser combined device of claim 1, wherein an attenuator of the plurality of attenuators is configured to linearly or discretely set energy values of the laser beam pulses in the operation modes.

13. The ophthalmic laser combined device of claim 1, wherein the aperture (15) or correction optics (32) are used to modify the profile energy distribution within the laser pulse in any of the operation modes.

14. The ophthalmic laser combined device of claim 1, further comprising at least one non-linear crystal (17A, 17B) configured to double the frequency of the laser beam pulse.

15. The ophthalmic laser combined device of claim 1, wherein the optical modules are configured to modify the profile of energy distribution within the laser beam pulse of the first and the second wavelength.

16. The ophthalmic laser combined device of claim 1 further comprising:
a red diode configured to project two optical paths, wherein the first path deflect from the beam splitter and the second path deflects from the mirror, the first and second paths converging into a focus point,
a laser filter (53) for filtering reflection of the laser pulse beam, and
an accessory lens mirror (55) configured to mirror the spot of the laser beam to a desired location (52), wherein when the device operates in the photodisruptor mode,
the laser beam source is configured to emit a short pulse of a length of about 5 ns in the infrared region at a wavelength of 1064 nm, wherein the short pulse goes through one of the plurality of attenuators,
a plate λ/2 is configured to rotate the polarization of the pulse,
a polarizer is configured to regulate output energy,
the polarization switch and the aperture are configured to be displaced from the optical path,
the laser pulse is configured to travels through the non-linear crystals without frequency doubling,
the pulse configured to travels from one of the non-linear crystals through one of the plurality of the pass filters for the infrared region, deflect from the first mirror, pass through correction optical system, and deflects from the second mirror;
the pulse is configured to go through the beam splitter, where a small portion thereof gets detected by an energymeter and a majority of the pulse goes through a shutter, through a small part to a large part of a telescope that expands the laser beam and deflects it via a dichroic mirror and a lens collects the laser pulse in a focus of the device.

17. The ophthalmic laser combined device of claim 1, further comprising:
a laser filter (53) for filtering reflection of the laser pulse beam, and
a red diode (44) for determining a site of the laser pulse, and
wherein when the device operates in the SLT mode,
the laser beam source is configured to emit a short pulse of a length of about 5 ns, wherein the short pulse goes through one of the plurality of attenuators,
plate λ/2 is configured to rotate polarization of the pulse,
a polarizer is configured to regulate output energy,
the non-linear crystals are configured to convert the frequency of the laser beam pulse from the first wavelength to the second wavelength as the polarization switch (16), which is transferred into the optical path;
the attenuator is configured to attenuate the pulse through the plurality of filters,
any portion of the first wavelength that was not converted in the non-linear crystal gets absorbed in the filter, deflects from the first mirror (20), goes past the correction optical system, and deflects again from the first mirror to the beam splitter,
the energometer is configured to detect a small portion of the pulse,
a larger portion of the pulse is configured to go through the shutter, through one of the plurality of telescope components,
the laser beam is configured to collimate in a first switch lens, travel through the correction optic to a second switch lens, and then travel to the large part of the telescope, deflects via the dichroic mirror, and get collected by the lens in the focal plane in a target spot of the laser beam,
an accessory lens is configured to mirror the target spot of the laser beam to a desired target,
the red diode is configured to be reflected in the focus where the spot of the red diode occurs,
the correction optic comprises shape of an aperture the laser beam is configured to travel to a first switch lens (31), travel through the correction optic (32) to a second switch lens (33), and then to the second telescope component (26B), the collimated laser beam is configured to deflect via the dichroic mirror (27) and gets collected by the lens (28) in the focal plane in a spot (54);

the red diode is configured to reflect to the focus (54) where the spot of the red diode occurs:

correction optics (32) comprise an aperture for enhancing the profile of the laser pulse.

\* \* \* \* \*